(12) United States Patent
Gordon

(10) Patent No.: US 6,261,261 B1
(45) Date of Patent: Jul. 17, 2001

(54) INFRARED HEATING DEVICE FOR PREWARMING IV SOLUTIONS

(76) Inventor: Lawrence O. Gordon, 6604 Sunny Hill Dr., Watauga, TX (US) 76148

( * ) Notice: Subject to any disclaimer, the term of this patent is extended or adjusted under 35 U.S.C. 154(b) by 0 days.

(21) Appl. No.: 09/478,279

(22) Filed: Jan. 5, 2000

Related U.S. Application Data

(60) Provisional application No. 60/114,756, filed on Jan. 5, 1999.

(51) Int. Cl.[7] ....................................................... A61F 7/12
(52) U.S. Cl. ............................................................ 604/113
(58) Field of Search ................................... 604/113, 114; 392/470, 472, 480, 485, 489, 490, 479; 219/528

Primary Examiner—Manuel Mendez
(74) Attorney, Agent, or Firm—Haynes and Boone, L.L.P.; John W. Montgomery

(57) ABSTRACT

An infrared device for prewarming IV solutions is provided with a cassette having a predetermined length of tubing connectable at an inlet to and IV solution source and an inlet connected to a device for infusion to a patient. An infrared energy-generating sheet is positioned in the cassette on or adjacent to the IV tubing or passage. The infrared energy sheet includes a fiberglass support grid, a layer formed on support matrix from a mixture of carbon and polymeric materials capable of producing infrared radiation in response to electrical current passed there through. A pair of electrical conduction power strips are attached along opposite sides of the matrix layer and are attached to input power terminals to provide the required current. The entire cassette may be held together with a glue or may be otherwise bonded or molded into a unit for convenient handling. An electrical power source is connected to the input power terminals for providing electrical power to be passed through the power strips and the layer of carbon and polymer mixture to generate infrared radiation that passes through the tubing or passage and penetrates into the IV solution as it passes through the cassette to be warmed thereby and infused into a patient at a desired temperature.

9 Claims, 3 Drawing Sheets

INFRARED HEATING DEVICE FOR PREWARMING IV SOLUTIONS

RELATED APPLICATION

This is a continuation application from the prior co-pending U.S provisional application No. 60/114,756 filed Jan. 5, 1999 with the same title and the same inventor, such prior application is incorporated herein, is relied upon for the benefit of priority and for all legitimate purposes and conversion of same to a non-provisional U.S. patent application is respectfully requested.

TECHNICAL FIELD OF THE INVENTION

The present invention relates to devices for preheating intravenous (IV) solutions prior to infusion into a patient, and more particularly to a disposable cassette having an infrared heating element electively powered for heating an IV solution prior to infusion to a patient.

BACKGROUND OF THE INVENTION

It has been found that in many medical situations it is advantageous to provide a patient with an intravenous infusion of a solution containing water, glucose, medicine, blood or components of blood, chemotherapy solutions, dyes, radiation-tracing materials and many other medical solutions for healing, therapy, diagnosis or other medical purposes. In may cases, the rate of infusion needs to be so rapid that the temperature of the solution may have a significant impact on the patient. Particularly, where the solution is administered at room temperature or below, which temperatures are significantly lower than the standard body temperature of 98.6 degrees.

In many situations, it has been found advantageous to heat a unit of solution, for example, a unit of plasma or a unit of blood prior to hanging the unit on the IV stand and attaching it to the IV tubing for infusion to the patient.

More recently, it has been found advantageous to provide disposable cassettes having metallic-resistance elements positioned adjacent to portions of an IV solution passage or enclosed tubing so that the solution is heated immediately prior to infusion to the patient. This advantageously allows maintenance of the solution at a cooler temperature, thereby preserving its usefulness, until immediately prior to infusion of the desired quantity at the prescribed rate. The metallic electrical resistance heater has certain drawbacks in the energy requirements for producing sufficient electrical resistance heating. Further, such devices have required special manufacturing techniques and materials that make the cost of production significant.

Thus, there is a need for an inexpensive, reliable infrared device for prewarming IV solutions immediately prior to infusing to patients.

SUMMARY OF THE INVENTION

Applicant has provided an infrared device for prewarming IV solutions that comprises a cassette having a predetermined length of IV tubing or a passage corresponding in size to the inside diameter of standard IV tubing. The passage has an inlet connectable to a source of IV solution and an outlet connectable to an IV infusion device, such as a needle or a catheter for infusing the prewarmed solution to the patient. At least one infrared energy-generating sheet is positioned in the cassette adjacent to the predetermined length of IV tubing. The infrared energy-generating sheet includes a fiberglass support grid and a matrix layer of a mixture of carbon and polymeric materials formed on the support grid for producing infrared radiation in response to electrical current passed through the matrix layer. A pair of electrical conduction power strips are placed along opposite sides of the matrix layer. Input power terminals are connected to the electrical conduction power strips and an electrical power source is connected to the input power terminals for providing electrical power to be passed through the power strips and thereby pass through the matrix layer of carbon and polymer mixture to generate infrared radiation. The cassette holds the infrared energy-generating sheet adjacent along the predetermined length of IV tubing so that the infrared energy is transferred to an IV solution carried through the tubing. Preferably, a temperature control microchip is provided operatively connected for sensing the temperature that results from infrared heating of the IV solution and automatically controls the electrical power to the infrared energy-generating sheet to maintain a desired rate of heating.

BRIEF DESCRIPTION OF THE DRAWINGS

The foregoing objects, advantages, and features, as well as other objects and advantages, will become more apparent with reference to the description and drawings below, in which like numerals represent like elements and in which.

DETAILED DESCRIPTION OF THE PREFERRED EMBODIMENTS

Figure 1:
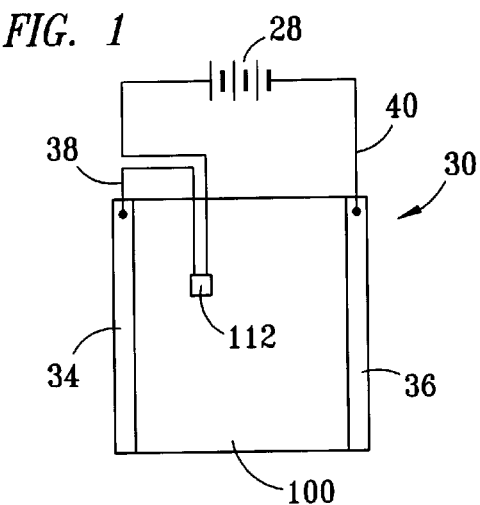
FIG. 1 schematically depicts an infrared heating layer according to one aspect of the present invention.
Figure 2:
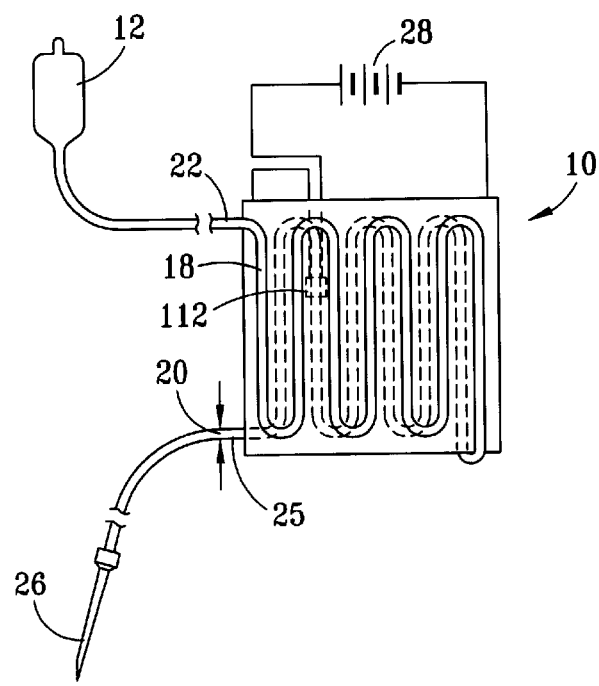
FIG. 2 schematically depicts a cassette having a predetermined length of IV tubing with the infrared heating element positioned therealong, and particularly the length of IV tubing is shown in a serpentine pattern formed on both sides of a small area of infrared energy-generating sheet, thereby facilitating heat transfer to the tubing.
Figure 3:
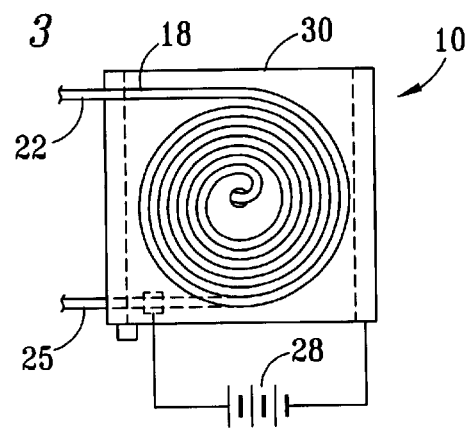
FIG. 3 shows an alternative embodiment in which a predetermined length of IV tubing is positioned in a spiral pattern along one side of a heating element passing through a central orifice and spiraling outwardly to an outlet.
Figure 4:
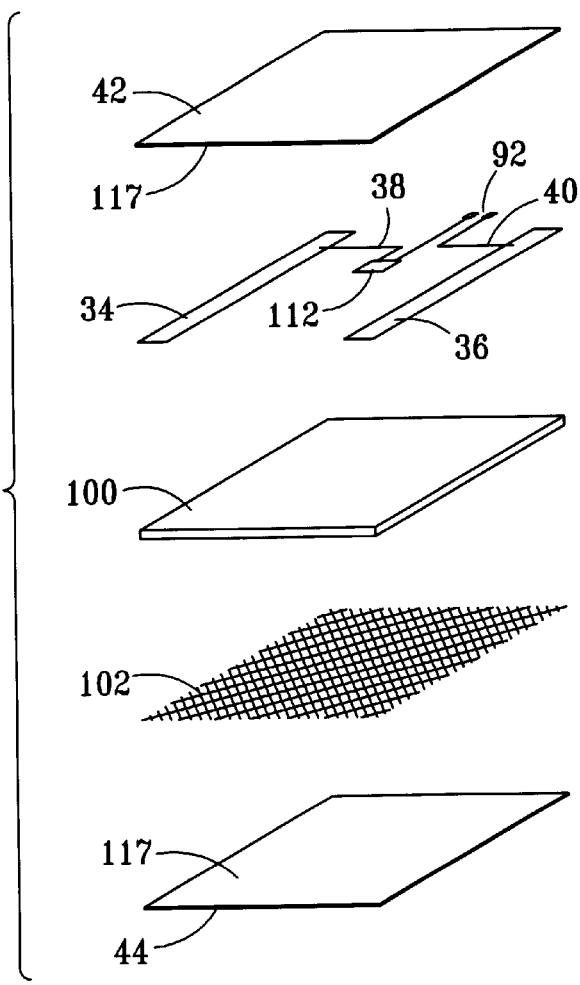
FIG. 4 shows a schematic depiction of an assembly view of an infrared heat-generating sheet according to the present invention.
Figure 5:
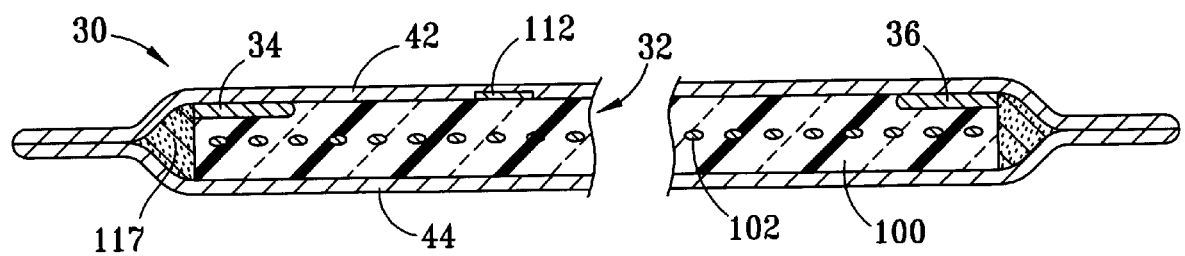
FIG. 5 shows a cross-section view of an infrared heating sheet formed according to assembly view FIG. 4.
Figure 6:
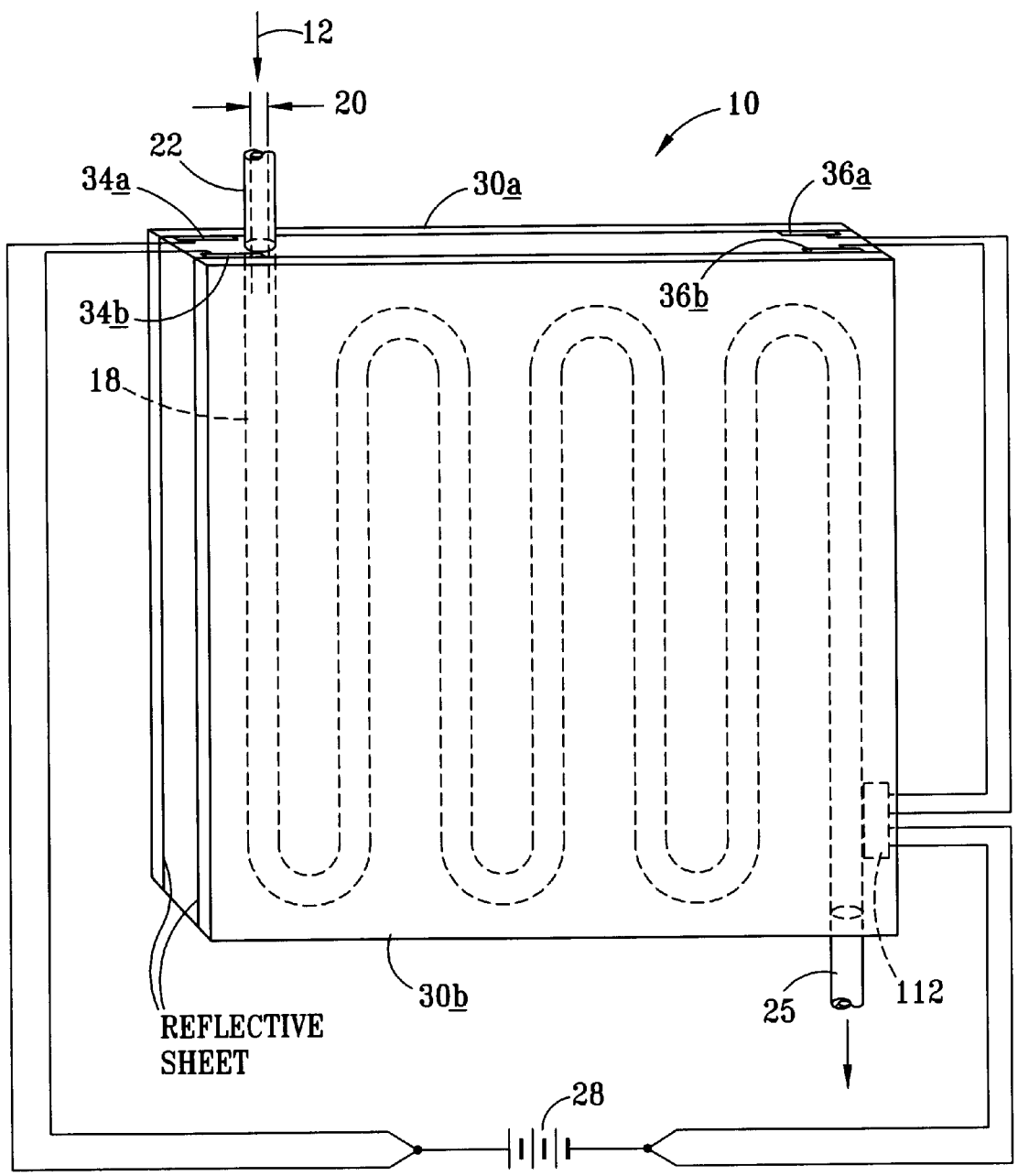
FIG. 6 is a schematic perspective view of an alternative embodiment of a cassette with a serpentine passage therethrough sandwiched between two heat-generating sheets, each having inwardly reflective material laminated on the outside thereof.

FIGS. 2 and 3 show an infrared device 10 for prewarming IV solutions 12 that comprises a cassette 14 having a predetermined length 16 of IV tubing 18 or a passage 18 corresponding in size to the inside diameter 20 of standard IV tubing. The passage 18 has an inlet 22 connectable to a source 12 of IV solution and an outlet connectable to an IV infusion device 26, such as a needle or a catheter for infusing the prewarmed solution to a patient. At least one infrared energy-generating sheet 30, as shown in FIGS. 1, 4 and 5, is positioned in the cassette adjacent to the predetermined length of IV tubing 18. The infrared energy-generating sheet 30 includes a fiberglass support grid 102 and a matrix layer 100 of a mixture of carbon and polymeric materials formed on the support grid for producing infrared radiation in response to electrical current passed through the matrix layer. A pair of electrical conduction power strips 34 and 36 are placed along opposite sides of the matrix layer. Input power terminals 92 are connected to the electrical conduction power strips 34 and 36 and an electrical power source 28 is connected to the input power terminals for providing electrical power to be passed through the power strips and thereby pass through the matrix layer of carbon and polymer mixture to generate infrared radiation. A portable storage battery, preferably less than 24 volts, as for example, 12 volts can be used as the power source 28. The cassette holds the infrared energy-generating sheet adjacent along the predetermined length of IV tubing so that the infrared energy is transferred to an IV solution carried through the tubing. Preferably, a temperature control microchip 112 is provided operatively connected for sensing the temperature that results from infrared heating of the IV solution and automatically controls the electrical power to the infrared energy-generating sheet to maintain a desired rate of heating. The matrix layer 100 on support grid 102 may be laminated between high temperature polymeric sheets 42 and 44 bonded together with bonding agent 117.

Other alterations and modifications of the invention will likewise become apparent to those of ordinary skill in the art upon reading the present disclosure, and it is intended that the scope of the invention disclosed herein be limited only by the broadest interpretation of the appended claims to which the inventors are legally entitled.

What is claimed is:

1. An infrared device for prewarming intravenous (IV) solutions comprising:
   (a) at least one cassette having a predetermined length of IV tubing passing therethrough with an inlet connectable to a source of IV solution and an outlet connectable to an IV infusion device;
   (b) at least one infrared energy-generating sheet positioned in said cassette adjacent to said predetermined length of IV tubing, said infrared energy sheet further comprising:
      i) a fiberglass support grid;
      ii) a matrix layer formed on said support grid, said matrix layer comprising a mixture of carbon and polymeric materials capable of producing infrared radiation in response to electrical current passed therethrough;
      iii) a pair of electrical conduction power strips along opposite sides of said layer;
      iv) a polymeric laminate enclosing said support grid, said matrix layer and said electrical conduction power strips, said polymeric laminate being substantially transparent to infrared radiation;
      v) input power terminals connected to said electrical conduction power strips; and
   (c) an electrical power source connected to said input power terminals for providing electrical power to be passed through said power strips and said matrix layer of carbon polymer mixture to generate infrared radiation therefrom.

2. An infrared device for prewarming IV solutions as in claim 1 further comprising:
   (a) predetermined area in said cassette on which said predetermined length of IV tubing is held in a serpentine configuration; and
   (b) said infrared energy-generating sheet operatively positioned adjacent said IV tubing co-terminus with said predetermined area.

3. An infrared device for prewarming IV solutions as in claim 1 further comprising a temperature control device operatively connected to said cassette for automatically terminating power to said power conducting strips when a temperature in said cassette exceeds a predetermined temperature.

4. An infrared device for prewarming IV solutions as in claim 3 wherein said temperature control device comprise a microchip circuit sensitive to a preselected temperature and connected to said input power for turning power "on" below said preselected temperature and "off" above said preselected temperature.

5. An infrared device for prewarming IV solutions as in claim 1 wherein said cassette further comprises:
   (a) said at least one heating element forming a bottom of said cassette; and
   (b) a top of said cassette spaced above said bottom and having another infrared radiation generating sheet positioned along said top for heating on said IV tubing from above.

6. An infrared heating device for prewarming IV solutions as in claim 1 further comprising:
   (a) a thermostat connected in said cassette for sensing a temperature indicative of the temperature of said IV solution to be warmed; and
   (b) a control circuit connected to said thermostat and said infrared heating element for controlling power to said infrared heating element so that a predetermined temperature range is maintained in said compartment.

7. An infrared heating device for prewarming IV solutions as in claim 7 wherein said control circuit comprises a temperature responsive microchip circuit preset for turning on and off at a predetermined temperature.

8. A disposable infrared warming device for prewarming IV solutions comprising:
   (a) at least one cassette having a length of fluid passage and an inlet for receiving IV solution warmed and an outlet for connecting to a patient to receive said warmed IV solution, said infrared heating device comprising:
   (b) at least one infrared energy-generating sheet positioned in said compartment adjacent to said length of IV passage, said infrared energy sheet further comprising:
      (i) a fiberglass support matrix;
      (ii) layer formed on said support matrix, said layer comprising a mixture of carbon and polymeric materials capable of producing infrared radiation in response to electrical current passed therethrough;
      (iii) a pair of electrical conduction power strips along opposite sides of said layer;
      (iv) polymeric laminate enclosing said support grid, said layer and said electrical conduction power strips, said polymeric laminate being substantially transparent to infrared radiation; and
   (c) an electrical power source connected to said input power strips for providing electrical power to be passed through said power strips and said layer of carbon polymer mixture to generate infrared radiation therefrom.

9. A disposable infrared IV prewarming device as in claim 9 further comprising:
   (a) a power cord adapted to connect to a movable power source; and
   (b) a portable battery power source movable from one patient to another as may be needed to connect to said disposable cassette infrared heating device.

* * * * *